(12) United States Patent
Fuisz et al.

(10) Patent No.: US 7,500,984 B2
(45) Date of Patent: Mar. 10, 2009

(54) PACIFIER WITH THIN-FILM RESERVOIR AND METHOD FOR USE THEREOF

(75) Inventors: Richard C. Fuisz, McLean, VA (US);
Joseph M. Fuisz, Washington, DC (US);
Tushar Misra, Leesburg, VA (US);
Pradeep Sanghvi, Schererville, IN (US)

(73) Assignee: MonoSol Rx, LLC, Portage, IN (US)

( * ) Notice: Subject to any disclaimer, the term of this patent is extended or adjusted under 35 U.S.C. 154(b) by 83 days.

(21) Appl. No.: 10/939,752

(22) Filed: Sep. 13, 2004

(65) Prior Publication Data
US 2006/0058845 A1    Mar. 16, 2006

(51) Int. Cl.
*A61J 11/00* (2006.01)
*A61J 7/00* (2006.01)
*A61J 17/00* (2006.01)

(52) U.S. Cl. ............... 606/236; 606/234; 604/77
(58) Field of Classification Search ......... 606/234–236; 215/11.1–11.5; 604/77
See application file for complete search history.

(56) References Cited

U.S. PATENT DOCUMENTS

| | | | | |
|---|---|---|---|---|
| 2,612,165 A * | 9/1952 | Szuderski | ............... | 606/236 |
| 3,610,248 A * | 10/1971 | Davidson | ............... | 606/236 |
| 3,825,014 A * | 7/1974 | Wroten | ............... | 606/236 |
| 4,128,445 A * | 12/1978 | Sturzenegger et al. | ....... | 156/64 |
| 5,072,842 A * | 12/1991 | White | ............... | 215/11.4 |
| 5,078,734 A * | 1/1992 | Noble | ............... | 604/77 |
| 5,176,705 A * | 1/1993 | Noble | ............... | 604/77 |
| 5,601,605 A | 2/1997 | Crowe et al. | | |
| D380,836 S * | 7/1997 | Fitzpatrick et al. | ....... | D24/194 |
| 6,203,566 B1 * | 3/2001 | Alanen et al. | ............... | 606/234 |
| 6,454,788 B1 | 9/2002 | Ashton | | |
| 6,552,024 B1 * | 4/2003 | Chen et al. | ............ | 514/252.16 |
| D476,085 S | 6/2003 | Dumont et al. | | |
| 6,575,999 B1 * | 6/2003 | Rohrig | ............... | 606/234 |
| D492,417 S | 6/2004 | Davis | | |
| 6,752,824 B2 * | 6/2004 | Yancy | ............... | 606/234 |
| 6,776,157 B2 | 8/2004 | Williams et al. | | |
| 2004/0044367 A1 | 3/2004 | Yancy | | |

* cited by examiner

*Primary Examiner*—Todd E Manahan
*Assistant Examiner*—Kathleen Sonnett
(74) *Attorney, Agent, or Firm*—Hoffman & Baron, LLP (57) ABSTRACT

The invention relates to a pacifier and nipple member for delivery of active ingredients into the oral cavity of an infant or patient. The pacifier includes a porous nipple member and a base member adapted to remain outside the oral cavity of the infant. The porous nipple member includes at least one reservoir or chamber therein for receiving a thin-film containing an active ingredient. The base member may be removably attached to the neck of the nipple member, or the nipple and base members may form a single unit. Reusable and disposable forms are disclosed.

19 Claims, 8 Drawing Sheets

PACIFIER WITH THIN-FILM RESERVOIR AND METHOD FOR USE THEREOF

FIELD OF THE INVENTION

The invention relates to a pacifier or nipple member for delivery of active ingredients into the oral cavity of an infant or patient. The pacifier has a porous nipple member and a reservoir or chamber therein for receiving a thin-film that contains an active ingredient. Active ingredients may include drugs and/or vitamins suitable for administration to infants or patients.

BACKGROUND OF THE RELATED TECHNOLOGY

It often is desirable to administer medications and/or vitamins to infants or patients in need thereof. Commonly used administration forms, however, experience certain known shortcomings. Due to an infant's natural propensity to suckle, pacifiers can be a useful tool for delivering such actives.

The prior art teaches pacifiers that have been modified to administer liquids and liquid medications to infants. Liquid medications may be difficult to insert into a pacifier, which can cause inaccuracy in the administration dosage. The present invention provides a pacifier that incorporates a thin-film dosage unit, thereby alleviating problems associated with the prior art.

SUMMARY OF THE INVENTION

In accordance with the present invention, there is provided a reusable pacifier for delivering an active ingredient to an infant or patient including: a porous nipple member having a nipple and a neck and having at least one reservoir therein for receiving a thin-film containing an active ingredient; and a base member removably attached to the neck of the nipple member and adapted to remain outside the oral cavity of the infant.

There also is provided a reusable pacifier for delivering an active ingredient to an infant or patient including: a porous nipple member having a nipple and a neck and having at least one reservoir therein; a thin-film housed in the reservoir, the film containing an active ingredient; and a base member removably attached to the neck of the nipple member and adapted to remain outside the oral cavity of the infant.

Another embodiment of the present invention provides a single-use pacifier for delivering an active ingredient to an infant or patient including: a base member adapted to remain outside the oral cavity of the infant, the base member including a shield having a concave side and a convex side; a porous nipple member disposed on the concave side of the base member, the nipple member having at least one reservoir therein; and a thin-film housed in the reservoir, the film containing an active ingredient.

In accordance with another embodiment of the present invention, there is provided a reusable pacifier for delivering an active ingredient to an infant or patient including: a base member adapted to remain outside the oral cavity of the infant, the base member including a shield having a concave side and a convex side; and a porous nipple member disposed on the concave side of the base member, the nipple member having at least one flap defining at least one chamber for receiving a thin-film containing an active ingredient.

Yet another embodiment of the present invention provides a baby bottle nipple for delivering an active ingredient to an infant including: a porous nipple member having a nipple and a neck and having at least one reservoir therein, wherein the neck is adapted to removably attach to a baby bottle; and a thin-film housed in the reservoir, the film containing an active ingredient.

The present invention also provides a method for delivering an active ingredient to an infant or patient including the steps of: providing a thin-film containing an active ingredient; providing a porous nipple member of a pacifier having a reservoir or chamber for receiving the thin-film containing an active; inserting the thin-film into the reservoir or chamber of the porous nipple member; and orally administering the pacifier to an infant or patient thereby allowing the thin-film to dissolve and release the active ingredient into the oral cavity.

BRIEF DESCRIPTION OF THE DRAWINGS

FIG. 5b is a cross-sectional view of the reservoir in the nipple member taken along line 5-5 of FIG. 5a;

DETAILED DESCRIPTION OF THE INVENTION

The present invention relates to delivery devices for drugs and other actives which are designed particularly for infants and patients such as the elderly, and those who have had surgery or other illnesses which prevent the ordinary dispensing of medication. The devices may be used for veterinary applications as well. The device of the present invention may be termed pacifiers or nipple members, since they are designed to administer the active through pores in the nipple member.

In particular, the present invention provides a pacifier or nipple unit for bottles, both of which are designed to deliver an active ingredient to a patient. The pacifier includes a porous nipple member and a base member. The pores in the nipple may be of any suitable shape and size. The nipple member includes a reservoir or other like chamber therein for receiving a thin-film that contains the active ingredient. The base member, which is adapted to remain outside the oral cavity of the infant or patient, may be removably attached to the nipple member. The pacifier may be a reusable or single-use device.

In one embodiment, the film containing active may be placed inside the hollow portion of the nipple and which by means of the nipple's porosity is in communication with saliva in the patient's oral cavity such that the saliva dissolves the film and releases the active into the oral cavity.

In another embodiment, as discussed herein, the nipple has a reservoir or chamber adapted to receive a film containing an active ingredient, the reservoir or chamber having pores which allow passage of the film and its active contents for release into the oral cavity.

Figure 1:
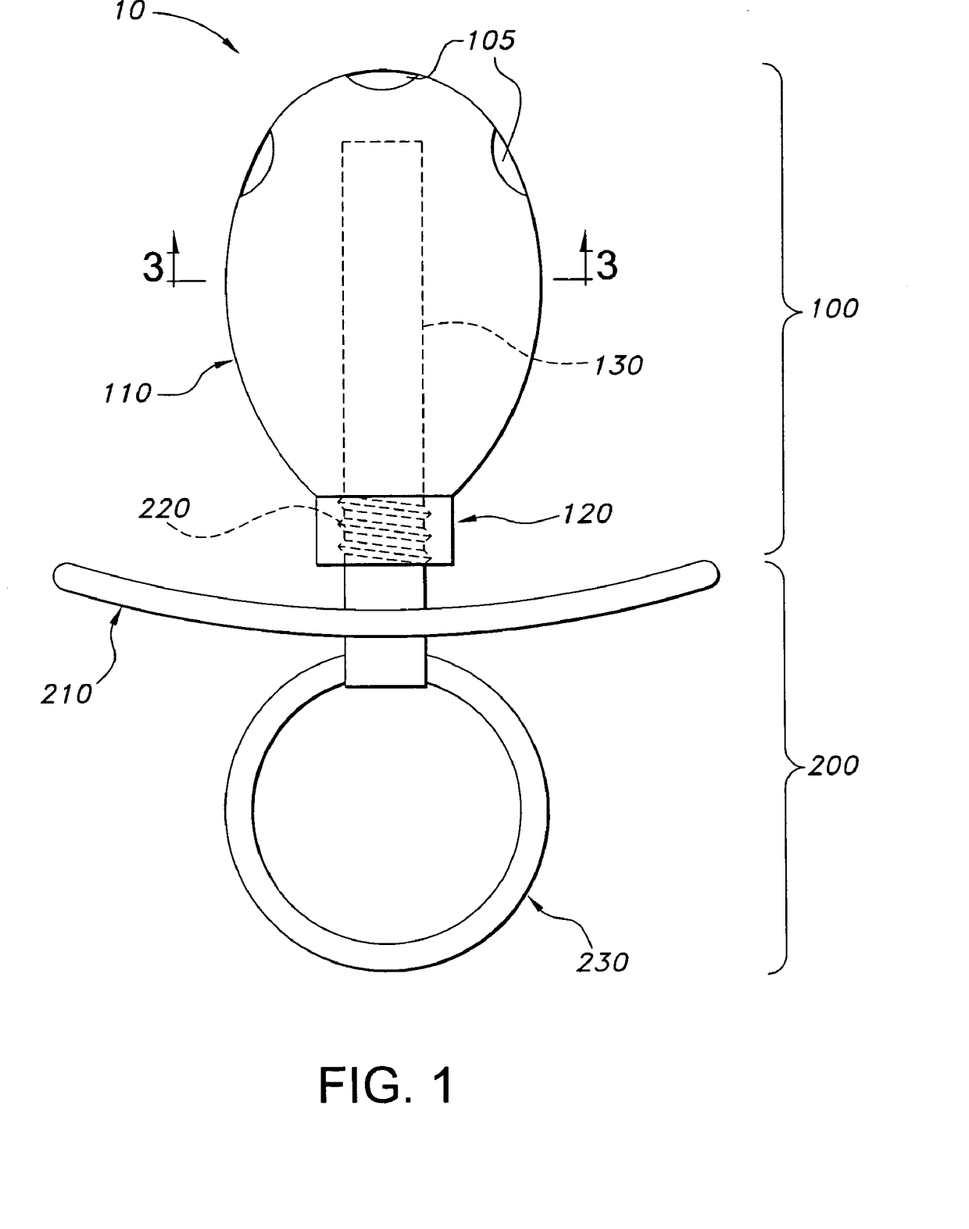
FIG. 1 is a side plan view of a reusable pacifier in accordance with an embodiment of the present invention.
Figure 5A:
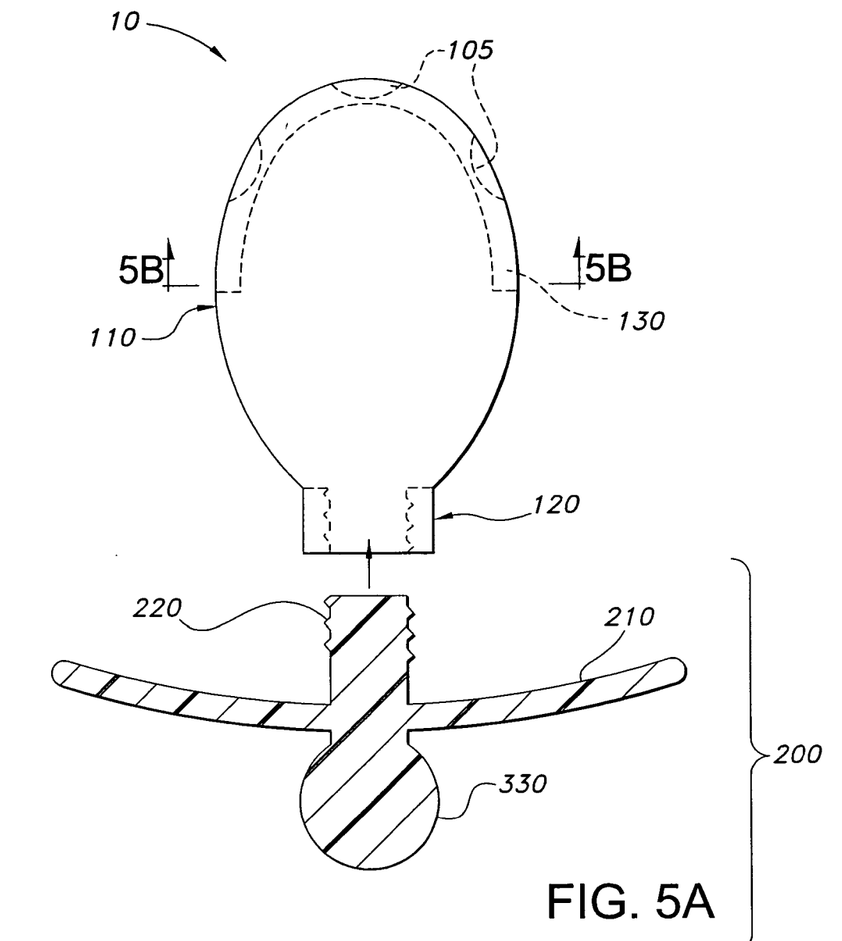
FIG. 5a is a side plan view of a reusable nipple member with a hollow reservoir in accordance with an embodiment of the present invention.
Figure 8:
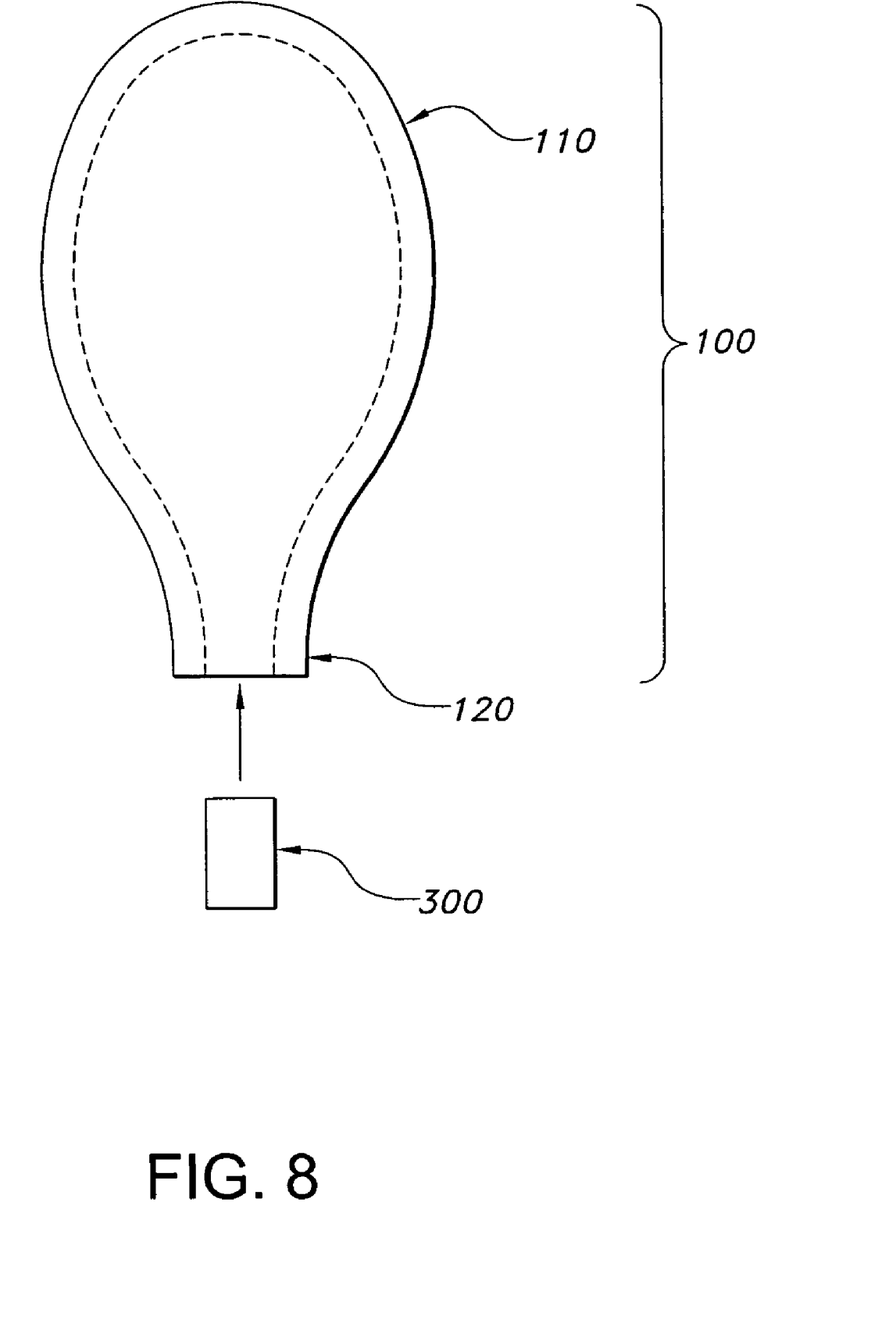
FIG. 8 is a side plan view of a solid plug shaped to fit within the neck of the nipple member in accordance with an embodiment of the present invention.

In accordance with some embodiments of the present invention, as shown in FIGS. 1 and 5a, the pacifier 10 includes a nipple member 100 and a base member 200. The nipple member 100 includes a nipple 110 wherein a rounded tip is contiguous with a neck 120. The nipple member 100 also has a reservoir therein 130 to receive a thin-film containing the active. Pores 105 permit the saliva to contact the film and the active ingredient to be released in the oral cavity. The pacifier 10 also may include a solid plug 300 shaped to fit within the neck 120 of the nipple member 100, as shown in FIG. 8.

The base member 200 includes a shield 210, which may have a concave side and a convex side. The base member 200 may include a handle member 230 or 330 that is pivotally attached to the convex side of the shield 210.

In a reusable embodiment, the base member 200 includes an attachment member 220 disposed on the concave side of the shield 210. The neck 120 of the nipple member 100 engages the attachment member 220 to removably attach the base member 200 to the nipple member 100. The attachment member 220 and neck 120 are attached via any mechanical connection known to those skilled in the art. For instance, the connection may be a threaded connection, as shown in FIG. 1. In this embodiment, the attachment member 220 and the neck 120 of the nipple member 100 each include threaded-mating portions. When the neck 120 engages the attachment member 220, a threaded connection is formed therebetween thereby removably attaching the nipple member 100 to the base member 200. The nipple member 100 may be removed from the base member 200 by unthreading the connection. This permits the user to reinsert a thin-film into the reservoir of the nipple member as desired. Other connections include, for example, but are not limited to, snap-fit or bayonet-lock fit.

Figure 2:
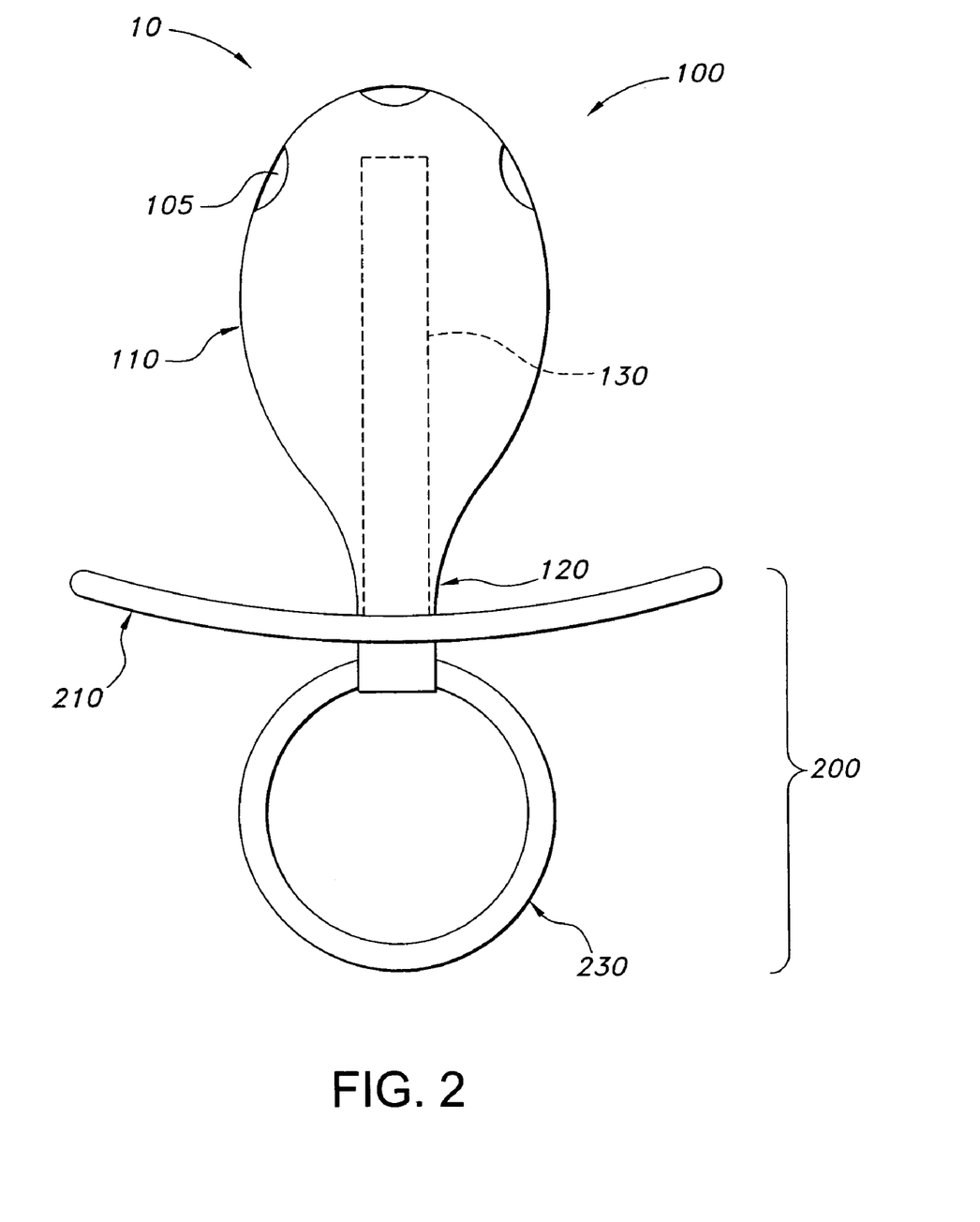
FIG. 2 is a side plan view of a single-use pacifier in accordance with an embodiment of the present invention.

In accordance with a single-use embodiment of the present invention, the nipple member 100 and base member 200 form a single molded device, as shown in FIG. 2. The nipple member and base member are a one-piece construction. Alternatively, the nipple member and base member may be molded separately and then attached to one another using a suitable nontoxic adhesive, press fit or other similar attachment means. The thin-film is inserted into reservoir 130 formed in the nipple portion of the pacifier during manufacture. Single-use embodiments are constructed to be disposable devices. As such, it may be desirable to produce the pacifier in a hermetically sealed package for sanitary reasons.

The nipple member of the pacifiers of the present invention may be constructed from any suitable resilient material that is acceptable for oral administration. Such materials are known to those skilled in the art. Suitable materials include, for example, rubber or plastic materials such as polyurethane, silicone, acrylics, polyethylene or polyvinyl chloride. The material is desirably porous or permeable to allow delivery of an active ingredient into the oral cavity of an infant or patient. For instance, the nipple member may contain a series of perforations or pores, such as pores 105 and slits 106, as shown in FIGS. 1, 2, 4, 5a, 6 and 7. The pores may be very small, as long as they are large enough to allow saliva to pass through the nipple to dissolve the film and release the active into the oral cavity. The pores, however, may be as large as desired to provide different release properties of the active. For example, it may be desirable to release some actives quickly, whereas other actives may work more effectively with a slower, controlled release. Moreover, the material may be porous throughout or selectively porous in certain regions to provide different release properties.

The active ingredient desirably is released from a thin-film contained in the reservoir or chamber of the nipple member. More specifically, the infant's or patient's sucking on the nipple allows saliva to reach the thin-film via the porous material of the nipple. The saliva dissolves the film and the active ingredient contained therein is released into the oral cavity. The material may further be translucent so that a user can visually determine when the film has dissolved. The size and shape of the nipple member can vary to accommodate different age groups or various animals for use in veterinary medicine.

Figure 3:
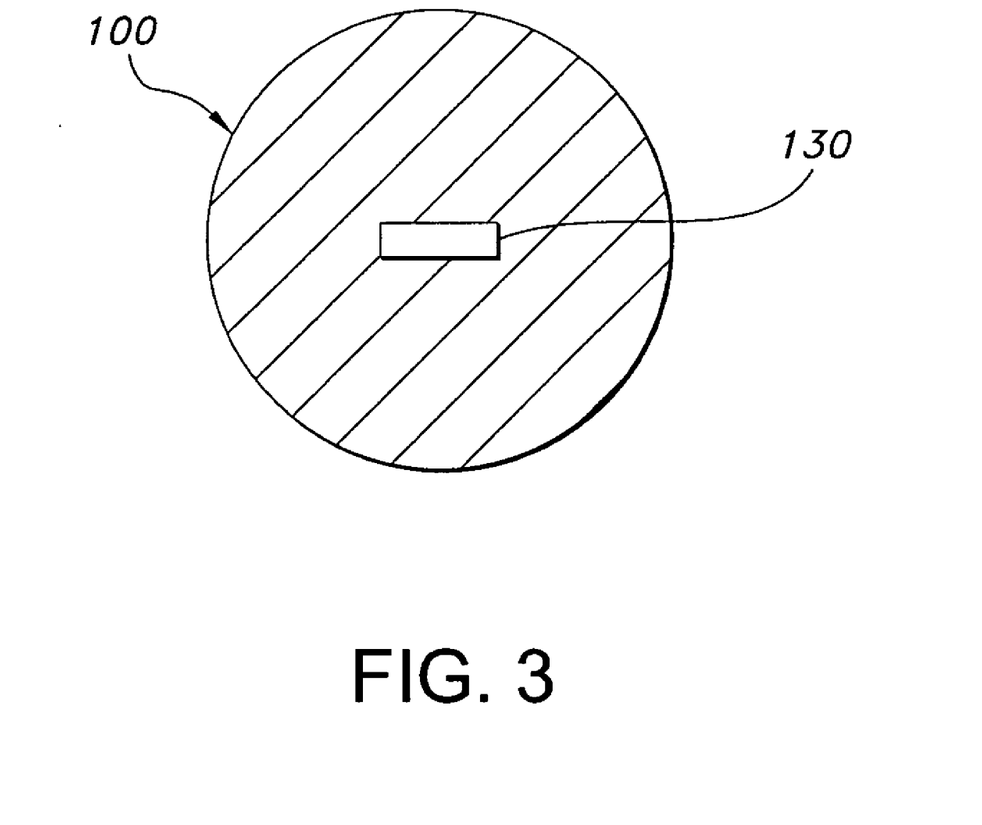
FIG. 3 is a cross-sectional view of the reservoir in the nipple member taken along line 3-3 of FIG. 1.
Figure 5B:
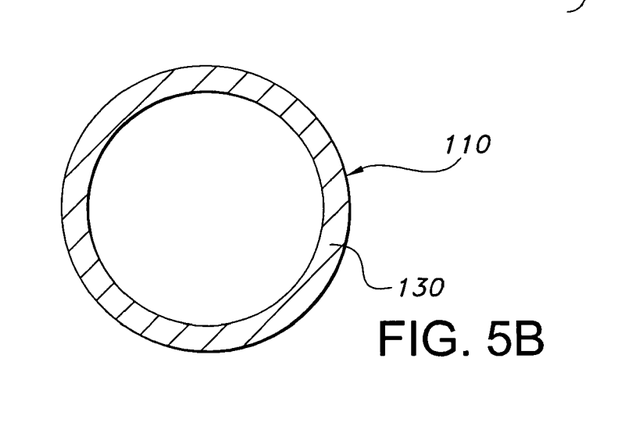

The reservoir 130 in the nipple member 100 is adapted to receive the thin-film. The reservoir may be such that the nipple member is hollow or a chamber sized to fit the piece of thin-film. In general, the films, when dried, have a thickness from about 3 μm to about 250 μm, or about 0.1 mils to about 10 mils. Desirably, the dried films will have a thickness of about 2 mils to about 8 mils, and more desirably, from about 3 mils to about 6 mils. Accordingly, the reservoir may have a thickness of slightly larger than about 0.1 mils to slightly larger than about 10 mils. The reservoir may have any shape suitable to receive thin-films as such. For example, as shown in FIG. 3, the reservoir 130 has a generally flat shape. As shown in FIG. 5b, the nipple member is generally hollow. The reservoir could have square or rounded edges.

In some embodiments, it may be desirable to include multiple reservoirs in the nipple member to house more than one film at a time. For example, it may be desirable to deliver more than one active ingredient to the infant or patient at the same time. In such case, different films each containing a different active may be inserted into separate reservoirs in the nipple member. Alternatively, it may be desirable to include a liquid, such as water, in one reservoir and a film in another reservoir. The liquid facilitates quick dissolution of the film as the infant or patient sucks on the nipple member. In other embodiments, the infant's or patient's saliva acts as the liquid source.

Figure 6:
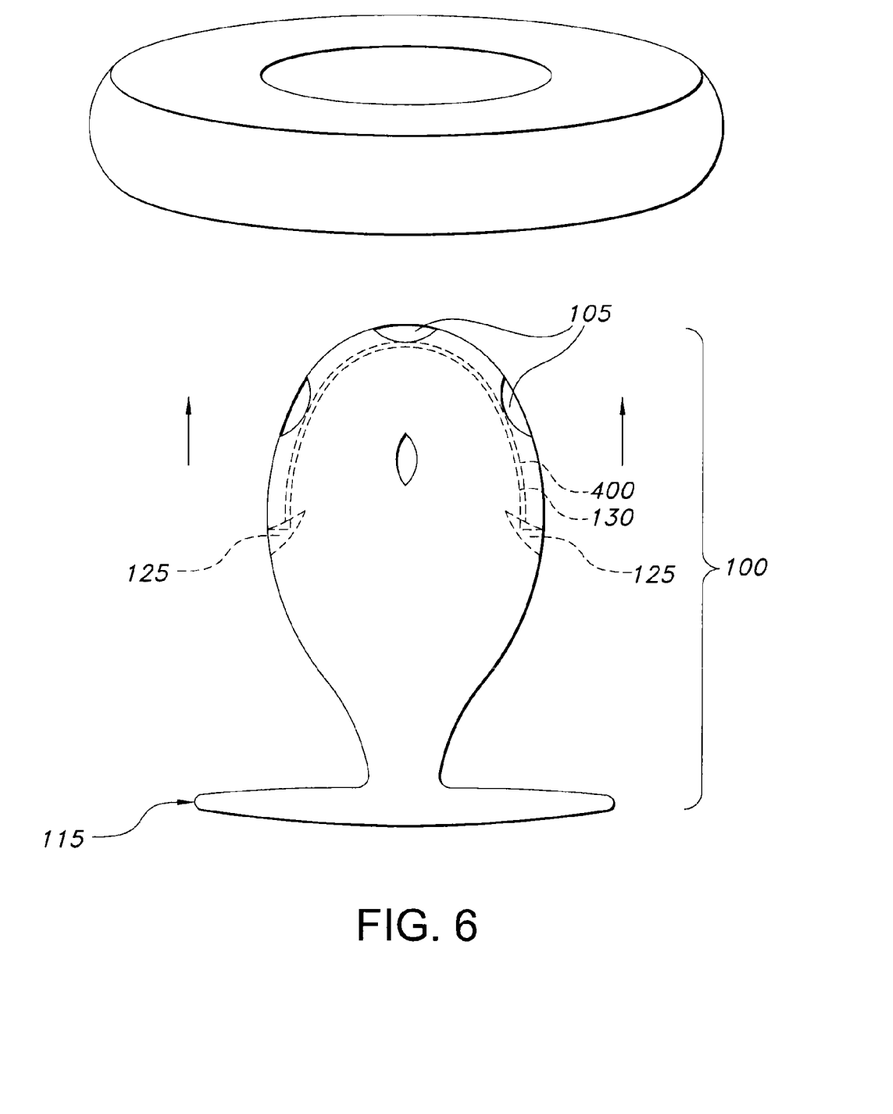
FIG. 6 is a side plan view of a nipple for a baby bottle in accordance with an embodiment of the present invention.
Figure 7:
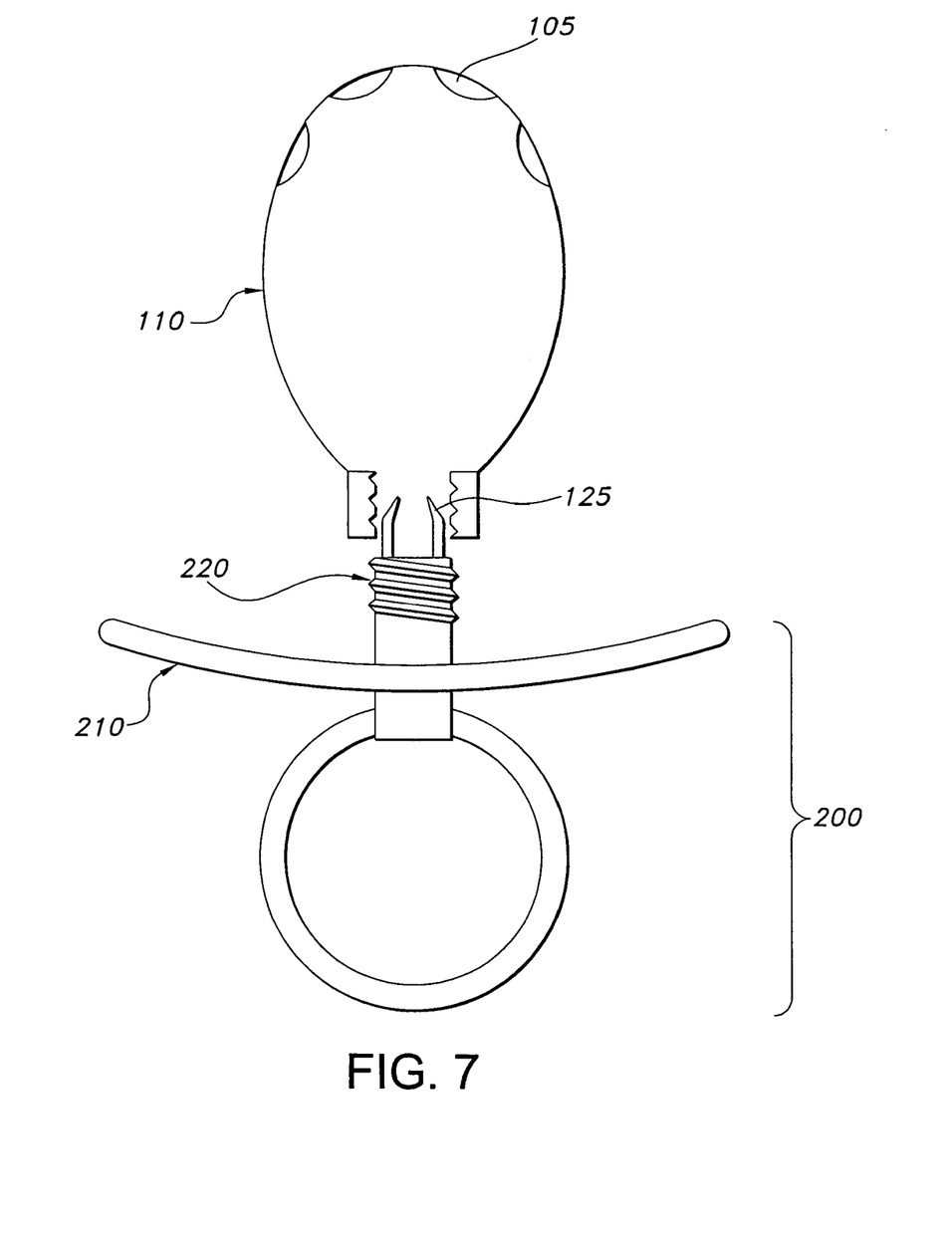
FIG. 7 is a side plan view of a reusable pacifier including retaining fingers on the base portion in accordance with an embodiment of the present invention.

The film may be free-standing in the reservoir or it may be held in-place by a retaining mechanism such as, but not limited to, clips or retaining fingers, as depicted in FIG. 6. As shown in FIG. 6, the retaining fingers 125 are disposed on the internal surface of the nipple member 100. Reservoir 130 may includes film 400, which is held against the internal surface of nipple member 100 by retaining fingers 125. Alternatively, the retaining fingers 125 may be disposed on the concave side of the base member 200, as shown in FIG. 7. The film 400 is thereby held in-place insider the reservoir once the nipple member is attached to the base member. Alternative retaining mechanisms are contemplated herein and would be known to those skilled in the art.

In some embodiments, the film may have a preformed curled shape to fit inside the nipple member and mate therewith. Alternatively, the film may be manufactured in a flat shape and curled for insertion into the nipple member. The curled film may be adapted to abut against part or the entire inner surface of the nipple member.

Figure 4:
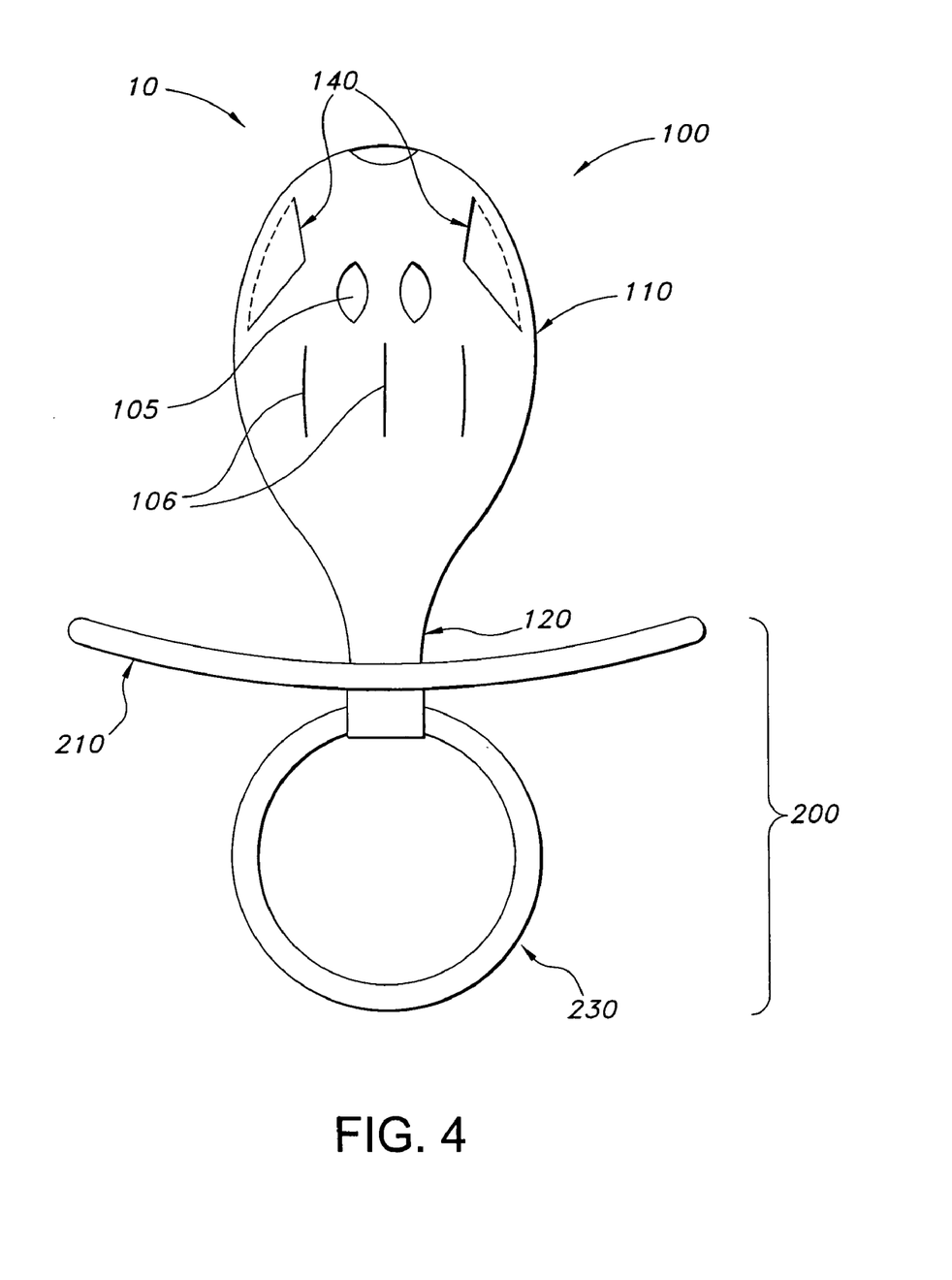
FIG. 4 is a side plan view of a pacifier with insertion flaps for accessing a reservoir or chamber in accordance with an embodiment of the present invention.

In accordance with another embodiment of the present invention, the nipple member of the pacifier contains at least one chamber created by a flap 140 in the external surface of the nipple, as shown in FIG. 4. For instance, one or more flaps 140 may be created by small cuts in the surface of the nipple member. A thin-film may be inserted into each of the flaps. As in the embodiments described above, the material of the nipple member is porous, thereby allowing release of the active from the film into the oral cavity.

Yet another embodiment of the present invention provides a nipple member for attachment to a baby bottle as shown in FIG. 6. As described in the embodiments above, the nipple member 100 may include a reservoir 130 adapted to receive a thin-film that contains an active ingredient. More specifically, the nipple member 100 is hollow as seen in FIG. 6. The film is inserted into the hollow nipple member via the base 115 of the nipple member and held in-place against the internal surface of the nipple by retaining fingers 125. Holding the film against the internal surface of the nipple as such allows saliva or liquid to reach the film quickly and thus may assist in quickly releasing the active. The nipple member similarly is formed of a porous or permeable material, as shown by pores 105 in FIG. 6. As the infant sucks on the nipple to obtain the liquid contained in the bottle, the infant's saliva and the liquid together act to dissolve the film thereby releasing the active ingredient into the oral cavity. The nipple member for the baby bottle may be disposable or reusable by reinserting another film as desired.

The active ingredients used in embodiments of the present invention may be any active suitable for administration to an infant or patient in need thereof. The active ingredient is desirably in a solid form, such as particulate, powder, dissolvable tablet, or most desirably a thin-film. The active ingredients include, without limitation, pharmaceutical and cosmetic actives, drugs, medicaments, antigens or allergens such as ragweed pollen, spores, microorganisms, seeds, mouthwash components, flavors, fragrances, enzymes, preservatives, sweetening agents, colorants, spices, vitamins and supplements and combinations thereof. Suitable active ingredients are more fully described in Applicants' co-pending U.S. application Ser. No. 10/074,272, filed Feb. 14, 2002, Ser. No. 10/768,809, filed Jan. 30, 2004, and Ser. No. 10/856,176, filed May 28, 2004, which are incorporated herein by reference in their entirety. Particularly suitable actives for delivery to infants include aspirin, benzocaine, lidocaine, diphenhydramine, simethicone, vitamins and cold and cough medications. Other suitable actives include medicaments for the treatment of pain, such as, for example, narcotic analgesics including fentanyl. Some embodiments are adapted for emergency or antidotal use and therefore include, for example, poison antidotes as actives. In other embodiments, it may be desirable to include mucosally active vaccines, such as, but not limited to, flu and west nile virus vaccines.

The thin-films which contain the active ingredients may be any film disclosed in U.S. application Ser. Nos. 10/074,272, 10/768,809 and 10/856,176, referred to above. These applications provide an extensive description of thin-films and methods for producing such films.

A variety of optional components also may be incorporated into the thin-films, as described in U.S. application Ser. Nos. 10/074,272, 10/768,809 and 10/856,176, referred to above. These may include, without limitation, anti-foaming agents, pigments, coloring agents, sweetening agents and flavoring agents, among others.

The present invention also is directed to methods for delivering the active ingredient to the oral cavity of an infant or patient. In accordance therewith, at least one thin-film containing an active ingredient is provided. The thin-film may be inserted into the reservoir or chamber of the porous nipple member. The film may be inserted through the neck of the nipple member. The film may be free-standing or clipped or retained in-place by a retaining member. In the single-use, or disposable, embodiments, the final pacifier device is manufactured with a base member. In the reusable embodiments, the porous nipple member may be attached to the base member to form the pacifier apparatus. Once the nipple member and base member are attached, or manufactured as a disposable pacifier, the pacifier may be orally administered to an infant or patient. The infant's or patient's saliva penetrates the porous nipple member and dissolves the thin-film. In accordance with some embodiments, the film's dissolution is facilitated by wetting the reservoir or chamber. The active ingredient contained in the film is thereby released into the oral cavity of the infant or patient.

Once the thin-film dissolves and the active is fully released, the pacifier may be removed from the oral cavity of the infant or patient. As discussed above, the material forming the nipple member may be translucent, thereby enabling the user to determine when the film is substantially consumed. In the reusable embodiments, the nipple member may be removed from the base member for administration of another thin-film as desired.

What is claimed is:

1. A pacifier for delivering an active ingredient to an infant or patient comprising:
   a base member comprising a shield;
   a porous nipple member attached to one side of said base member, said nipple member having a wall defining at least one chamber, an inner surface of said wall being in contiguous contact with said chamber, said chamber containing a dissolvable thin-film comprising an active ingredient; and
   said thin-film being held-in-place by a retaining mechanism for said dissolvable thin-film, said retaining mechanism having a first retaining finger outwardly projecting from said inner surface and having an unattached end, wherein said first retaining finger continuously holds said dissolvable thin-film against said inner surface.

2. The pacifier of claim 1, further comprising at least one flap located on the external surface of the nipple to permit positioning of the film in said chamber.

3. The pacifier according to claim 1, wherein said porous nipple member further comprises a neck and said shield comprises a concave side and a convex side, wherein said shield has an attachment member disposed on the concave side of said shield for engaging said nipple member.

4. The pacifier according to claim 3, wherein said neck and said attachment member comprise threaded-mating portions.

5. The pacifier according to claim 3, wherein said neck and said attachment member comprise a snap-fit.

6. The pacifier according to claim 3, wherein said neck and said attachment member comprise a bayonet-lock fit.

7. The pacifier according to claim 3, wherein said base member further comprises a handle attached to the convex side of said shield.

8. The pacifier according to claim 3, further comprising a solid plug shaped to fit within said neck of said nipple member.

9. The pacifier according to claim 1, wherein said thin-film has a thickness of about 0.1 mils to about 10 mils.

10. The pacifier according to claim 1, wherein said active ingredient is selected from the group consisting of: pharmaceutical agents; cosmetic agents; drugs; medicaments; antidotes; vaccines; antigens or allergens; mouthwash components; flavors; fragrances; enzymes; preservatives; sweetening agents; colorants; spices; vitamins; and combinations thereof.

11. The pacifier according to claim 1, wherein said active ingredient is selected from the group consisting of: aspirin; benzocaine; lidocaine; diphenhydramine; simethicone; vitamins; cold and cough medications; and combinations thereof.

12. The pacifier according to claim 1, wherein said active ingredient comprises fentanyl.

13. The pacifier according to claim 1, wherein said thin-film has a curled shape.

14. The pacifier of claim 1, wherein there is further included a hermetically sealed package containing said pacifier.

15. The pacifier of claim 1, wherein said retaining mechanism further comprises a second retaining finger outwardly projecting from said inner wall and having an unattached end, wherein said unattached ends of said first retaining finger and said second retaining finger are spaced apart so that said unattached end of said first retaining finger does not come into contact with said unattached end of said second retaining finger.

16. A method for delivering an active ingredient to an infant or patient comprising the steps of:
    providing a thin-film comprising an active ingredient;
    providing a porous nipple member of a pacifier comprising a wall defining at least one chamber, an inner surface of said wall being in contiguous contact with said chamber and having at least one retaining mechanism, said retaining mechanism having a first retaining finger projecting outwardly from said inner surface and having at least one unattached end;
    inserting the thin-film into the at least one chamber of the porous nipple member, wherein said first retaining finger is configured to continuously hold said dissolvable thin-film against said inner surface; and
    orally administering the pacifier to an infant or patient thereby allowing the thin-film to dissolve and release the active ingredient into the oral cavity.

17. The method according to claim 16, wherein the method further includes the step of wetting the chamber containing the thin-film to facilitate dissolution of the film.

18. The method according to claim 17, wherein the porous nipple member further contains a reservoir or chamber which houses a liquid.

19. The method according to claim 16, further comprising the step of attaching the porous nipple member to a base member, wherein the nipple member comprises a neck that engages an attachment member disposed on the base member.

* * * * *